United States Patent [19]

Das et al.

[11] Patent Number: 4,525,479

[45] Date of Patent: Jun. 25, 1985

[54] 7-OXABICYCLOHEPTANE SUBSTITUTED THIOCARBAMATE PROSTAGLANDIN ANALOGS USEFUL AS CARDIOVASCULAR AGENTS

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 527,070

[22] Filed: Aug. 29, 1983

[51] Int. Cl.³ .................... A61K 31/34; C07D 307/00
[52] U.S. Cl. .................... 514/469; 549/463
[58] Field of Search .................... 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane substituted thiocarbamate prostaglandin analogs are provided having the structural formula

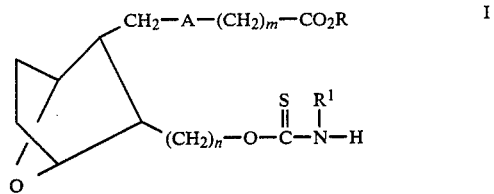

and including all stereoisomers thereof.

The compounds are cardiovascular agents useful, for example, in the treatment of thrombolytic disease.

14 Claims, No Drawings

7-OXABICYCLOHEPTANE SUBSTITUTED THIOCARBAMATE PROSTAGLANDIN ANALOGS USEFUL AS CARDIOVASCULAR AGENTS

DESCRIPTION OF THE INVENTION

The present invention relates to 7-oxabicycloheptane thiocarbamate prostaglandin analogs which are cardiovascular agents useful, for example, in the treatment of thrombolytic disease. These compounds have the structural formula

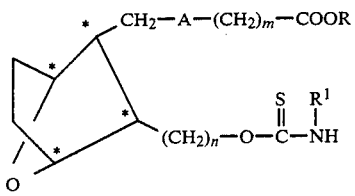

and including all stereoisomers thereof, wherein A is a single bond, —CH=CH—, $CH_2$ or $(CH_2)_2$, m is 0 to 8 but when A is —CH=CH—, m is at least 1, n is 1 to 5, R is H or lower alkyl, and $R^1$ is lower alkyl, aryl, aralkyl, lower alkoxy, aralkoxy or cycloalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$" and "$(CH_2)_n$" includes a straight or branched chain radical having from 1 to 8 carbons in the normal chain in the case of "$(CH_2)_m$" and 1 to 5 carbons in the normal chain in the case of "$CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

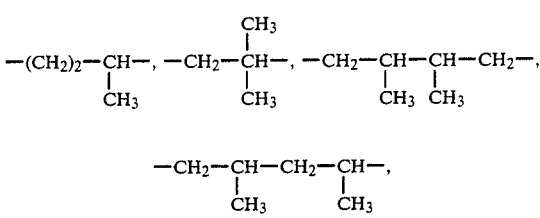

and the like.

Preferred are those compounds of formula I wherein A is CH=CH, m is 2 to 4, R is H, n is 1, and $R^1$ is lower alkyl, aryl, such as phenyl or aralkyl such as benzyl.

The various compounds of the invention may be prepared as outlined below.

A. Where n is 1 and A is CH=CH

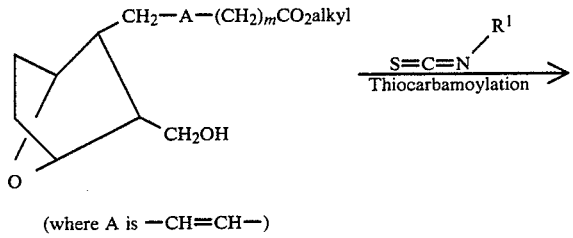

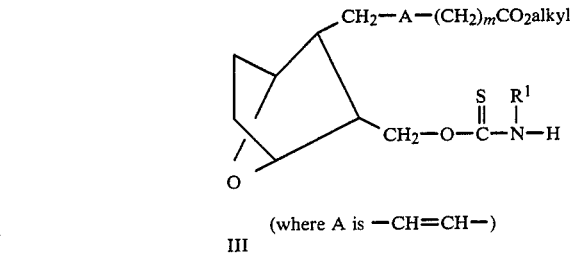

B. Where n is 1 and A is $CH_2$, $(CH_2)_2$ or a single bond

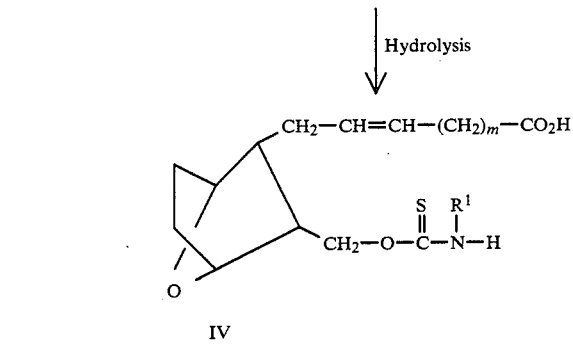

-continued

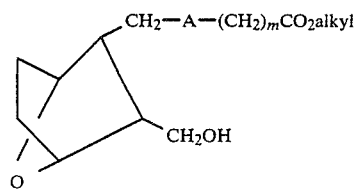 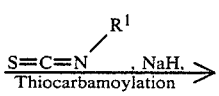 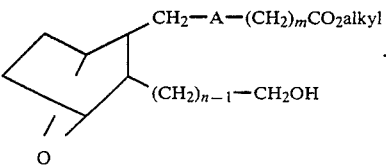

IIA (where A is —CH$_2$,
—(CH$_2$)$_2$ or a single
bond)

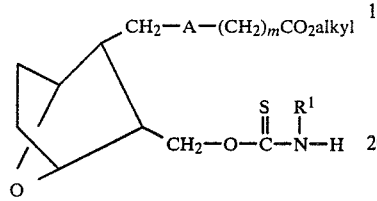

IIIA (where A is —CH$_2$,
—(CH$_2$)$_2$— or a
single bond)

↓ Hydrolysis

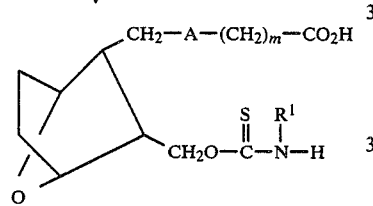

IVA (where A is CH$_2$, (CH$_2$)$_2$,
or a single bond)

C. Where n is 2 to 5

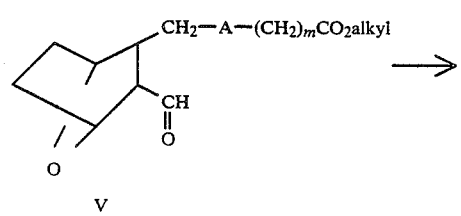

V

[Wittig (C$_6$H$_5$)$_3$P=CHOMe, Hydrolysis,

H$_3$O$^+$] repeated (n − 1) times

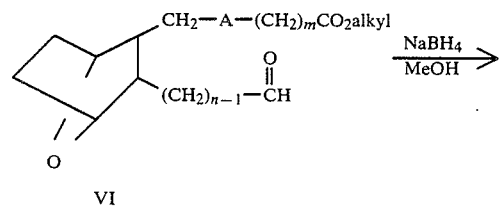

VI $\xrightarrow{\text{NaBH}_4}{\text{MeOH}}$

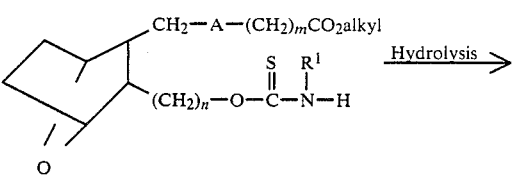

VII

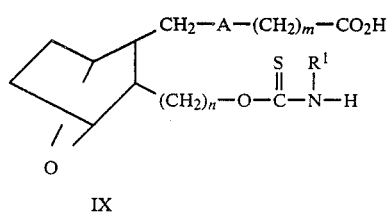

VIII

Hydrolysis →

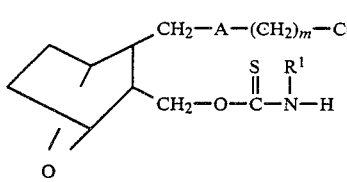

IX

As seen in the reaction sequences identified as "A" and "B", compounds of the invention wherein n is 1, that is,

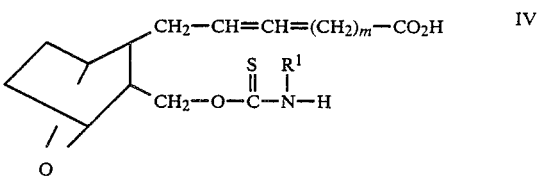

IV

IVA (wherein A is CH$_2$, (CH$_2$)$_2$ or a single bond)

may be prepared by reacting the starting lower alkyl ester II (A is CH=CH) or IIA (A is a single bond, CH$_2$ or (CH$_2$)$_2$) (prepared as described in U.S. Pat. No. 4,143,054) with an isothiocyanate of the structure

 A in the presence of a base such as NaH, KH, pyridine, triethylamine, NaOCH$_3$, or KOt-Bu, preferably NaH, in the presence of an inert organic solvent such as benzene, toluene, tetrahydrofuran or methylene chloride, and preferably in an inert atmosphere employing a molar ratio of II or IIA:A of within the range of from about 0.5:1 to about 1:1. The resulting alkyl ester III or IIIA is then subjected to hydrolysis to form the acid IV or IVA by treating the esters with a base such as lithium hydroxide, followed by neutralization with an acid such as dilute hydrochloric acid or oxalic acid.

In the reaction sequence identified as "C", the aldehyde III or IIIA is used to prepare aldehyde VI (where n is 2-5) by carrying out a homologation sequence, such as a Wittig reaction with $(C_6H_5)_3P=CHOMe$ followed by hydrolysis, (n-1) times. The aldehyde VI (where n is 2-5) is thus carried on to the compounds of this invention where n is 2-5, that is

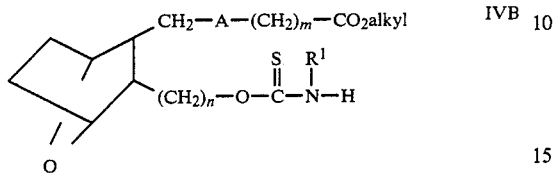   IVB by reduction employing a reducing agent such as sodium borohydride in a solvent such as methanol to form the alcohol VII

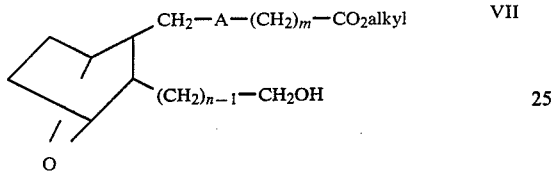   VII which is reacted with an isothiocyanate A in the presence of a base and solvent as described hereinbefore to form the compound of the invention VIII

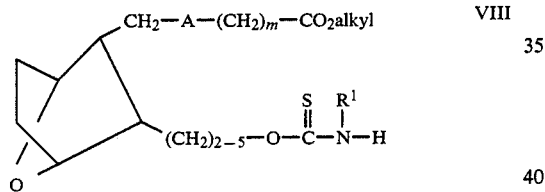   VIII

Compound VIII may then be hydrolyzed to the corresponding acid IX.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

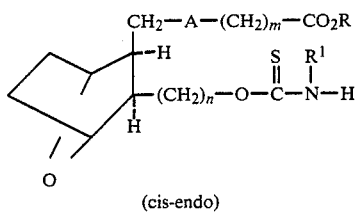

(cis-endo)

-continued

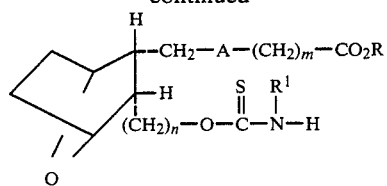

(cis-exo)

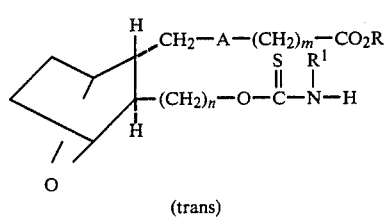

(trans)

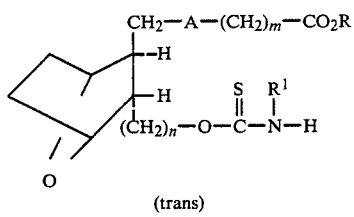

(trans)

The nucleus in each of the compounds of the invention is depicted as

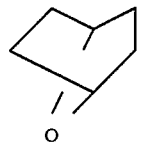

for matter of convenience; it will also be appreciated that the nucleus in the compounds of the invention may be depicted as

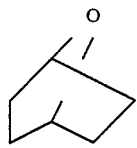

The compounds of this invention are cardiovascular agents useful as platelet aggregation inhibitors such as arachidonic acid-induced platelet aggregation, e.g., for treatment of thrombolytic disease, such as coronary or cerebral thromboses. In addition, the compounds of the invention are useful in inhibiting bronchoconstriction such as associated with asthma and as well as in treating peripheral vascular disease. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention.

EXAMPLE 1

[1β,2α(5Z),3α,4β]-7-[3-[[[(Phenylmethyl)amino]thioxomethoxy]methyl]-7-oxabicyclo[2.2.1]hept-2-yl]-5-heptenoic acid, methyl ester To a slurry of 72 mg of 50% sodium hydride in mineral oil in 2 ml dry benzene (1.5 mmole, 2 eq.) at 0° C. was added a solution of 200 mg (0.75 mmole) [1β,2α(5Z),3α,4β]-7-[3-(hydroxymethyl)-7-oxabicyclo[2.2.1]hept-2-yl]-5-heptenoic acid, methyl ester (prepared as described in U.S. Pat. No. 4,143,054) in 2 ml dry benzene. The mixture was stirred for 15 minutes at 0° C. under argon, and then 178.5 mg benzylisothiocyanate (1.5 mmole, 2 eq.) was added. The reaction mixture was stirred for 30 minutes at 25° C., then quenched with 1.5 ml of 1N HCl, poured into 5 ml of brine, extracted with three 20 ml portions of $CH_2Cl_2$, dried over anhydrous $MgSO_4$ and concentrated to give a crude yellow oil. This was purified by flash chromatography on a LPS-1 silica gel column, eluting with 20% EtOAc/hexanes to give 64 mg of title compound as a yellow oil.

EXAMPLE 2

[1β,2α(5Z),3α,4β]-7-[3-[[[(Phenylmethyl)amino]thioxomethoxy]methyl]-7-oxabicyclo[2.2.1]hept-2-yl]-5-heptenoic acid To 64 mg of Example 1 ester (0.17 mmole) in 4 ml THF and 1 ml $H_2O$ was added dropwise 1.7 ml of 1M LiOH solution at 25° C. The mixture was stirred at 25° C. for 18 hours and then concentrated. The residue was diluted with 5 ml $H_2O$, acidified with saturated oxalic acid solution to pH 3, extracted with three 20 ml portions of ether, dried over anhydrous $MgSO_4$ and concentrated to give a yellow oil.

The above oil was purified by flash chromatography on a LPS-1 silica gel column, eluting with 2% $MeOH/CH_2Cl_2$ to give 50 mg of title compound as an oil. This was dried under high vacuum for 2 days.

TLC of title compound: Silica gel; 5% $MeOH/CH_2Cl_2$; $R_f \sim 0.46$.

Anal. Calcd (included 0.66 mole $H_2O$) for $C_{22}H_{29}NO_4S$: C, 63.62; H, 7.37; N, 3.37; S, 7.72. Found: C, 63.62; H, 7.17; N, 3.37; S, 7.47.

EXAMPLE 3

[1β,2α(5Z),3β,4β]-7-[3-[[Butylamino]thioxomethoxy]methyl]-7-oxabicyclo[2.2.1]hept-2-yl]-5-heptenoic acid, methyl ester To a slurry of 144 mg of 50% sodium hydride in mineral oil in 4 ml dry benzene (3 mmole, 2 eq.) at 0° C. is added a solution of 402 mg (1.5 mmole) [1β,2α(5Z),3α,4β]-7-[3-(hydroxymethyl)-7-oxabicyclo[2.2.1]hept-2-yl]-5-heptenoic acid methyl ester (prepared as described in U.S. Pat. No. 4,143,054) in 4 ml dry benzene. After stirring for 30 minutes at 0° C. under argon, 345 mg of n-butyl isothiocyanate (3 mmole) is added dropwise. The reaction mixture is warmed to room temperature and stirred for an additional 30 minutes, whereupon it is quenched with HCl, poured into brine and extracted (3×) with $CH_2Cl_2$, dried over $MgSO_4$ and concentrated. The concentrate is chromatographed on a silica gel column (flash chromatography, LPS-1 silica gel) and eluted with 50% ethylacetate in hexane to give the title thiocarbamate.

EXAMPLE 4

[1β,2α(5Z),3β,4β]-7-[3-[[Butylamino]thioxomethoxy]methyl]-7-oxabicyclo[2.2.1]hept-2-yl]-5-heptenoic acid To a solution of 400 mg of the Example 3 thiocarbamate in 6 ml of distilled THF is added with stirring 2 ml of 1N aqueous lithium hydroxide solution and 0.5 ml of water. The reaction mixture is stirred at room temperature for 6 hours, whereupon it is diluted with methylene chloride and washed thoroughly with saturated salt solution. The organic layer is dried over anhydrous magnesium sulfate and concentrated in vacuo to give 330 mg of title acid (90% crude yield). Further purification by chromatography on a silica gel column (CC-7 silica gel) and elution with 50% ethyl-acetate in methylene chloride gives analytically pure title acid.

EXAMPLE 5

(1β,2β,3α,4β)-7-[3-[[(Phenylamino)thioxomethoxy]methyl]-7-oxabicyclo[2.2.1]hept-2-yl]heptanoic acid

A.

(1β,2β,3α,4β)-7-[3-(Hydroxymethyl)-7-oxabicyclo[2.2.1]hept-2-yl]heptanoic acid, methyl ester To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25° C., filtered through a celite plug and evaporated to provide 730 mg (90%) of the title A compound.

B.

(1β,2β,3α,4β)-7-[3-[[(Phenylamino)thioxomethoxy]methyl]-7-oxabicyclo[2.2.1]hept-2-yl]heptanoic acid Following the procedure of Example 1 except substituting phenylisothiocyanate for benzylisothiocyanate, the title product is obtained.

EXAMPLE 6

[1β,2α(5Z),3α,4β]-7-[3-[[(Cyclohexylamino)thioxomethoxy]methyl]-7-oxabicyclo[2.2.1]hept-2-yl]-5-heptenoic acid Following the procedure of Examples 1 and 2, except substituting cyclohexylisothiocyanate for benzylisothiocyanate, the title compound is obtained.

EXAMPLE 7

[1β,2α(5Z),3β,4β]-7-[3-[[(Methoxymethylamino)thiox-omethoxy]methyl]-7-oxabicyclo[2.2.1]hept-2-yl]-5-heptenoic acid Following the procedure of Examples 3 and 4 except substituting methoxymethylisothiocyanate for n-butylisothiocyanate, the title compound is obtained.

EXAMPLE 8

(1β,2β,3α,4β)-7-[3-[[(Benzylamino)thioxomethoxy]methyl]-7-oxabicyclo[2.2.1]hept-2-yl]heptanoic acid Following the procedure of Example 5 except substituting benzylisothiocyanate for phenylisothiocyanate, the title compound is obtained.

EXAMPLE 9

[1β,2α(5Z),3α,4β]-7-[3-[[(Phenoxymethylamino)thioxomethoxy]methyl]-7-oxabicyclo[2.2.1]hept-2-yl]-5-heptenoic acid Following the procedure of Examples 1 and 2 except substituting phenoxymethylisothiocyanate for benzylisothiocyanate, the title compound is obtained.

EXAMPLE 10

[1β,2α(5Z),3β,4β]-7-[3-[[[p-Ethylphenylamino]thioxomethoxy]methyl]-7-oxabicyclo[2.2.1]hept-2-yl]-5-heptenoic acid Following the procedure of Examples 3 and 4 except substituting p-ethylphenylisothiocyanate for n-butylisothiocyanate, the title compound is obtained.

EXAMPLE 11

(1β,2β,3α,4β)-7-[3-[[[Cyclopentylmethylamino]thioxomethoxy]methyl]-7-oxabicyclo[2.2.1]hept-2-yl]heptanoic acid Following the procedure of Example 5 except substituting cyclopentylmethylisothiocyanate for phenylisothiocyanate, the title compound is obtained.

EXAMPLE 12

[1β,2α(5Z),3α,4β]-7-[3-[[[Phenethylamino]thioxomethoxy]methyl]-7-oxabicyclo[2.2.1]hept-2-yl]-5-heptenoic acid Following the procedure of Examples 1 and 2 except substituting phenethylisothiocyanate for benzylisothiocyanate, the title compound is obtained.

EXAMPLE 13

[1β,2α(5Z),3α,4β]-7-[3-[[(Butylamino)thioxomethoxy]ethyl]-7-oxabicyclo[2.2.1]hept-2-yl]-5-heptanoic acid

A.
[1β,2α(5Z),3α,4β]-7-[3-(2-Oxo)ethyl-7-oxabicyclo[2.2.1]hept-2-yl]-5-heptenoic acid, methyl ester Into a dry 1000 ml round bottom 3-necked flask containing a stir bar was added dried 12.9 g (37.7 mmoles) methoxymethyltriphenylphosphonium chloride ((C₆H₅)₃P⁺—CH₂OCH₃Cl⁻) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH₄Cl, and extracted with ether (4×200 ml). The combined ether phases were washed with NaCl, saturated solution, and dried (MgSO₄) and concentrated to yield a yellow oil in a white crystalline solid (phosphine oxide). The white solid was triturated with EtOAc and purified by chromatography on an LPS-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl-7-oxabicyclo[2.2.1]hept-2-yl]-5-heptenoic acid, methyl ester and (C) 1β,2α(5Z),3α,4β]-7-[3-(2,2-dimethoxy)ethyl-7-oxabicyclo[2.2.1]-hept-2-yl]-5-heptenoic acid methyl ester.

Compounds (B) and (C) are each treated with trifluoroacetic acid to convert each to compound (C).

B.
[1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH₄ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO₃, saturated NaCl and dried (MgSO₄). The ether is evaporated to yield the title B compound.

C.
[1β,2α(5Z),3α,4β]-7-[3-[[(Butylamino)thioxomethoxy]ethyl]-7-oxabicyclo[2.2.1]hept-2-yl]-5-heptenoic acid Following the procedure of Example 1 except substituting the above part B alcohol for the alcohol used in Example 1, and substituting butylisothiocyanate for benzylisothiocyanate, the title compound is obtained.

EXAMPLE 14

[1β,2α(5Z),3β,4β]-7-[3-[[(Butylamino)thioxomethoxy]ethyl]-7-oxabicyclo[2.2.1]hept-2-yl]-5-heptenoic acid Following the procedure of Example 13, except substituting [1β,2α(5Z),3β,4β]-7-[3-formyl-7-oxabicyclo[2.2.1]hept-2yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 15

(1β,2β,3α,4β)-7-[3-[[(Butylamino)thioxomethoxy]ethyl]-7-oxabicyclo[2.2.1]hept-2-yl]heptanoic acid Following the procedure of Example 13 except substituting (1β,2β,3α,4β)-7-[3-formyl-7-oxabicyclo[2.2.1]hept-2-yl]-5-heptanoic acid, methyl ester for [1β,2α(5Z),3β,4β]-7-[3-formyl-7-oxabicyclo[2.2.1]hept-2-yl]-5-heptenoic acid, methyl ester, the title compound is obtained.

EXAMPLE 16

[1β,2α(5Z),3α,4β]-7-[3-[[(Cyclohexylamino)thioxomethoxy]ethyl]-7-oxabicyclo[2.2.1]hept-2-yl]-5-heptenoic acid Following the procedure of Example 13 except substituting cyclohexylisothiocyanate for benzylisothiocyanate, the title compound is obtained.

EXAMPLE 17

[1β,2α(5Z),3β,4β]-7-[3-[[(Methoxymethylamino)thioxomethoxy]ethyl]-7-oxabicyclo[2.2.1]hept-2-yl]-5-heptenoic acid Following the procedure of Example 14 except substituting methoxymethylisothiocyanate for butylisothiocyanate, the title compound is obtained.

EXAMPLE 18

(1β,2β,3α,4β)-7-[3-[[(Benzylamino)thioxomethoxy]ethyl]-7-oxabicyclo[2.2.1]hept-2-yl]heptanoic acid Following the procedure of Example 15 except substituting benzylisothiocyanate for butylisothiocyanate, the title compound is obtained.

EXAMPLE 19

[1β,2α(5Z),3α,4β]-7-[3-[[(Phenoxymethylamino)thioxomethoxy]ethyl]-7-oxabicyclo[2.2.1]hept-2-yl]-5-heptenoic acid Following the procedure of Example 13 except substituting phenoxymethylisothiocyanate for butylisothiocyanate, the title compound is obtained.

EXAMPLE 20

[1β,2α(5Z),3β,4β]-7-[3-[[[p-Ethylphenylamino]thioxomethoxy]ethyl]-7-oxabicyclo[2.2.1]hept-2-yl]-5-heptenoic acid Following the procedure of Example 14 except substituting p-ethylphenylisothiocyanate for butylisothiocyanate, the title compound is obtained.

EXAMPLE 21

(1β,2β,3α,4β)-7-[3-[[[Cyclopentylmethylamino]thioxomethoxy]ethyl]-7-oxabicyclo[2.2.1]hept-2-yl]heptanoic acid Following the procedure of Example 15 except substituting cyclopentylmethylisothiocyanate for butylisothiocyanate, the title compound is obtained.

EXAMPLE 22

[1β,2α(5Z),3α,4β]-7-[3-[[(Phenethylamino)thioxomethoxy]ethyl]-7-oxabicyclo[2.2.1]hept-2-yl]-5-heptenoic acid Following the procedure of Example 13 except substituting phenethylisothiocyanate for butylisothiocyanate, the title compound is obtained.

EXAMPLE 23

[1β,2α(5Z),3α,4β]-7-[3-[[(Butylamino)thioxomethoxy]butyl]-7-oxabicyclo[2.2.1]hept-2-yl]-5-heptenoic acid

A.

[1β,2α(5Z),3α,4β]-7-[3-(3Oxo)propyl-7-oxabicyclo[2.2.1]hept-2-yl]-5-heptenoic acid, methyl ester Following the procedure of Example 13, part A except substituting [1β,2α(5Z),3α,4β]-7-[3-(2-Oxo)ethyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title A compound is obtained.

B.

[1β,2α(5Z),3α,4β]-7-[3-(4-Oxo)propyl-7-oxabicyclo[2.2.1]hept-2-yl]-5-heptenoic acid, methyl ester Following the procedure of Example 13, part A, except substituting the aldehyde from part A above, for [1β,2α(5Z),3α,4β]-7-[3-formyl-7-oxabicyclo[2.2.1]hept-2-yl]-5-heptenoic acid, methyl ester, the title B aldehyde is obtained.

C.

[1β,2α(5Z),3α,4β]-7-[3-3-(4-Hydroxybutyl)-7-oxabicyclo[2.2.1]hept-2-yl]-5-heptenoic acid, methyl ester Following the procedure of Example 13, part B, except substituting the title B aldehyde for [1β,2α(5Z),3α,4β]-7-[3-(2-oxo)ethyl-7-oxabicyclo[2.2.1]hept-2-yl]-5-heptenoic acid, methyl ester, the title C alcohol is obtained.

D.

[1β,2α(5Z),3α,4β]-7-[3-[[(Butylamino)thioxomethoxy]butyl]-7-oxabicyclo[2.2.1]hept2-yl]-5-heptenoic acid Following the procedure of Example 1, except substituting the above part C alcohol for the alcohol used in Example 1 and substituting butylisothiocyanate for benzylisothiocyanate, the title compound is obtained.

EXAMPLE 24

[1β,2α(5Z),3α,4β]-7-[3-[[(Cyclohexylamino)thioxomethoxy]butyl]-7-oxabicyclo[2.2.1]hept-2-yl]-5-heptenoic acid Following the procedure of Example 23 except substituting cyclohexylisothiocyanate for butylisothiocyanate, the title compound is obtained.

EXAMPLE 25

[1β,2α(5Z),3α,4β]-7-[3-[[(Methoxmethylamino)thioxomethoxy]butyl]-7-oxabicyclo[2.2.1]hept-2-yl]-5-heptenoic acid Following the procedure of Example 23 except substituting methoxymethylisothiocyanate for butylisothiocyanate, the title compound is obtained.

EXAMPLE 26

(1β,2β,3α,4β)-7-[3-[[(Benzylamino)thioxomethoxy]butyl]-7-oxabicyclo[2.2.1]hept-2-yl]heptanoic acid Following the procedure of Example 25 except substituting benzylisothiocyanate for butylisothiocyanate and substituting (1β,2β,3α,4β)-7-[3-(2-oxo)ethyl-7-oxabicyclo[2.2.1]hept-2-yl]heptanoic acid, methyl ester for the [1β,2α(5Z),3α,4β]-7-[3-(2-oxo)ethyl-7-oxabicyclo[2.2.1]hept-2-yl]-5-heptenoic acid, methyl ester, the title compound is obtained.

EXAMPLE 27

[1β,2α(5Z),3α,4β]-7-[3-[[(Phenoxymethylamino)thioxomethoxy]butyl]-7-oxabicyclo[2.2.1]hept-2-yl]-5-heptenoic acid Following the procedure of Example 23 except substituting phenoxymethylisothiocyanate for butylisothiocyanate, the title compound is obtained.

EXAMPLE 28

[1β,2α(5Z),3α,4β]-7-[3-[[[[(3-Fluorophenyl)methyl]amino]thioxomethoxy]methyl]-7-oxabicyclo[2.2.1]hept-2-yl]-5-heptenoic acid, methyl ester To a suspension of prewashed sodium hydride (108 mg, 4.5 mmole) in 5 ml of benzene, cooled in an ice-water bath was added dropwise a solution of [1β,2α(5Z),3α,4β]-7-[3-(hydroxymethyl)-7-oxabicyclo[2.2.1]hept-2-yl]-5-heptenoic acid, methyl ester (605 mg, 2.25 mmole) in 5 ml of benzene. After 10 minutes, m-fluorobenzylisothiocyanate (700 mg, 4.5 mmole, 2 eq.) was added dropwise. The reaction mixture was allowed to stir at 0° to room temperature for 18 hours, whereupon it was quenched by addition of 1N aq. HCl solution. Extractive workup in methylene chloride gave a crude oil.

This oil was purified by flash chromatography on a LPS-1 silica gel column, eluting with 20% EtOAc/hexanes to give 190 mg of title ester as an oil.

EXAMPLE 29

[1β,2α(5Z),3α,4β]-7-[3-[[[[(3-Fluorophenyl)methyl]amino]thioxomethoxy]methyl]-7-oxabicyclo[2.2.1]hept-2-yl]-5-heptenoic acid To 190 mg of Example 28 ester (0.43 mmole) in 8 ml THF and 2 ml H₂O was added dropwise 4.3 ml of 1M LiOH solution at 25° C. The mixture was stirred at 25° C. for 18 hours, then concentrated. The residue was diluted with 10 ml H₂O and acidified to pH 3 with saturated oxalic acid solution, extracted with three 30 ml portions of ether, dried over anhydrous MgSO₄, and concentrated to give a yellow oil.

This oil was purified by flash chromatography on a LPS-1 silica gel column, eluting with 2% MeOH/CH₂Cl₂ to give 115 mg of title product as an oil.

This was dried under high vacuum for 2 days at 25° C.

TLC of title compound: Silica gel; 5% MeOH/CH₂Cl₂; $R_f \sim 0.45$.

Anal. Calcd (includes 0.89 mole H₂O) for C₂₂H₂₈FNO₄S: C, 60.,39; H, 6.86; N, 3.20; S, 7.33; F, 4.34. Found: C, 60,39; H, 6.61, N, 3.22; S, 7.23; F, 4.41.

EXAMPLE 30

[1β,2α(5Z),3α,4β]-7-[3-[[[(Cyclohexylmethyl)amino]thioxomethoxy]methyl]-7-oxabicyclo[2.2.1]hept-2-yl]-5-heptenoic acid, methyl ester To a suspension of prewashed sodium hydride (168 mg, 7 mmole) in 10 ml of benzene was added at 0°–5° C., dropwise, a solution of [1β,2α(5Z),3α,4β]-7-[3-(hydroxymethyl)-7-oxabicyclo[2.2.1]hept-2-yl]-5-heptenoic acid, methyl ester (885 mg, 3.3 mmole) in 5 ml of benzene. After 10 minutes, cyclohexane methylisothiocyanate (1.1 g, 7 mmole) was added dropwise. The reaction was stirred at 0°–5° C. for 1 hour and quenched by addition of 1N HCl. Extractive work up in CH₂Cl₂ gave a crude oil which was purified by flash chromatography on a LPS-1silica gel column, eluting with 20% EtOAc/hexanes to give 380 mg of title ester as an oil.

EXAMPLE 31

[1β,2α(5Z),3α,4β]-7-[3-[[[(Cyclohexylmethyl)amino]thioxomethoxy]methyl]-7-oxabicyclo[2.2.1]hept-2-yl]-5-heptenoic acid To 380 mg of Example 30 ester (0.9 mmole) in 16 ml THF and 4 ml H₂O was added dropwise 9 ml of 1M LiOH solution at 25° C. The mixture was stirred at 25° C. for 18 hours, then concentrated. The residue was diluted with 20 ml H₂O and acidified to pH 3 with saturated oxalic acid solution, extracted with three 50 ml portions of ether, dried over anhydrous MgSO₄, and concentrated to give a yellow oil which was purified on a LPS-1 silica gel column eluting with 2% MeOH/CH₂Cl₂ to give 230 mg of title acid as an oil.

This oil was dried under high vacuum at 25° C. for 2 days.

TLC of title acid: Silica gel; 5% MeOH/CH₂Cl₂; $R_f \sim 0.45$.

Anal. Calcd for C₂₂H₃₅NO₄S: C, 64.51; H, 8.61; N, 3.41; S, 7.82. Found: C, 64.04; H, 8.79; N, 3.56; S, 7.70.

What is claimed is:

1. A compound having the structural formula

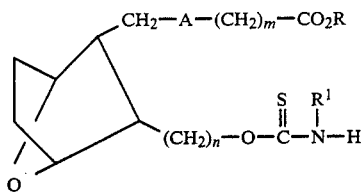

and including all stereoisomers thereof;

wherein A is CH═CH, a single bond, CH₂ or (CH₂)₂; m is 0 to 8 but where A is CH═CH, m is at least 1; n is 1 to 5; R is H or lower alkyl; and R¹ is lower alkyl; lower alkyl including a halo-substituent an alkoxy substituent, an aryl substituent, an alkyl-aryl substituent, a haloaryl substituent, a cycloalkyl substituent or an alkylcycloalkyl substituent; aryl; aryl including a lower alkyl substituent, a halogen substituent or a lower alkoxy substituent; aralkyl; lower alkoxy; aralkoxy; cycloalkyl; or cycloalkyl including 1 or 2 halogen substituents, 1 or 2 lower alkyl substituents or 1 or 2 lower alkoxy substituents;

as employed above the term lower alkyl or alkyl by itself or as part of another group contains up to 12 carbons;

as employed above the term aryl by itself or as part of another group refers to monocyclic or bicyclic aromatic groups containing from 6 to 10 carbons in the ring portion;

as employed above the term cycloalkyl by itself or as part of another group refers to saturated cyclic hydrocarbon groups containing 3 to 12 carbons; and wherein (CH₂)ₘ and (CH₂)ₙ may be substituted by one or more alkyl substituents.

2. The compound as defined in claim 1 having the formula

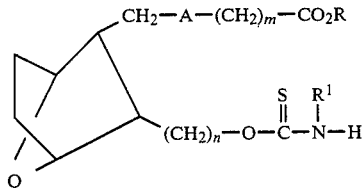

wherein R is hydrogen, R¹ is lower alkyl, alkoxy or aralkoxy, including all stereoisomers thereof.

3. The compound as defined in claim 1 wherein n is 1.

4. The compound as defined in claim 2 wherein A is CH=CH.

5. The compound as defined in claim 4 wherein $R^1$ is butyl, pentyl, hexyl or heptyl.

6. The compound as defined in claim 1 having the name [1β,2α(5Z),3α,4β]-7-[3-[[[(phenylmethyl)amino]-thioxomethoxy]methyl]-7-oxabicyclo[2.2.1]hept-2-yl]-5-heptenoic acid or the methyl ester thereof, including all stereoisomers thereof.

7. The compound as defined in claim 1 having the name [1β,2α(5Z),3α,4β]-7-[3-[[[[(3-fluorophenyl)methyl]amino]thioxomethoxy]methyl]-7-oxabicyclo[2.2.1]hept-2-yl]-5-heptenoic acid or the methyl ester thereof, including all stereoisomers thereof.

8. The compound as defined in claim 1 having the name [1β,2α(5Z),3α,4β]-7-[3-[[[(cyclohexylmethyl)amino]thioxomethoxy]methyl]-7-oxabicyclo[2.2.1]hept-2-yl]-5-heptenoic acid or the methyl ester thereof, including all stereoisomers thereof.

9. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

10. The method as defined in claim 9 wherein said compound is administered in an amount within the range of from about 1 to about 100 mg/kg.

11. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

12. A method of inhibiting platelet aggregation which comprises administering to a mammalian host an effective amount of a compound as defined in claim 1 or a pharmaceutically acceptable salt thereof.

13. A method of inhibiting bronchoconstriction associated with asthma, which comprises administering to a mammalian host an effective amount of a compound as defined in claim 1 or a pharmaceutically acceptable salt thereof.

14. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,525,479

DATED : June 25, 1985

INVENTOR(S) : Jagabandhu Das et al.

It is certified that error appears in the above—identified patent and that said Letters Patent is hereby corrected as shown below:

Column 9, line 53, "heptanoic" should read --heptenoic--.
Column 12, line 15, "[3-3-(4-" should read --[3-(4- --.
Column 14, line 32, after "halo-substituent" insert a comma --,--

Signed and Sealed this

Twenty-ninth Day of October 1985

[SEAL]

Attest:

Attesting Officer

DONALD J. QUIGG

Commissioner of Patents and
Trademarks—Designate